United States Patent
Masumoto

(10) Patent No.: US 8,788,288 B2
(45) Date of Patent: Jul. 22, 2014

(54) SYSTEM AND METHOD FOR PROMOTING UTILIZATION OF MEDICAL INFORMATION

(75) Inventor: Jun Masumoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 678 days.

(21) Appl. No.: 12/760,947

(22) Filed: Apr. 15, 2010

(65) Prior Publication Data
US 2010/0268060 A1   Oct. 21, 2010

(30) Foreign Application Priority Data

Apr. 16, 2009  (JP) ................................. 2009-100384
Mar. 31, 2010  (JP) ................................. 2010-083140

(51) Int. Cl.
*G06Q 50/22*  (2012.01)
*G06Q 50/24*  (2012.01)

(52) U.S. Cl.
USPC .................................................. 705/3; 705/2

(58) Field of Classification Search
CPC .............................. G06Q 50/22; G06Q 50/24
USPC ........................................................ 705/2–3
See application file for complete search history.

(56) References Cited

U.S. PATENT DOCUMENTS

| | | | | |
|---|---|---|---|---|
| 7,421,100 | B2 * | 9/2008 | Truyen | 382/128 |
| 2004/0101186 | A1 * | 5/2004 | Tong et al. | 382/132 |
| 2007/0237380 | A1 * | 10/2007 | Iwase et al. | 382/131 |
| 2008/0267481 | A1 * | 10/2008 | Nakamura | 382/131 |

* cited by examiner

*Primary Examiner* — Michael Fuelling
(74) *Attorney, Agent, or Firm* — Sughrue Mion, PLLC

(57) ABSTRACT

A server computer judges a region represented by an image obtained by an imaging apparatus. The server computer generates intelligent information regarding body tissue which can be estimated based on the imaged region, and registers the generated intelligent information in an intelligent information database. Workstations and the like that assist the work of medical workers execute filtering processes depending on the users thereof, to limit the range of assistance, the range of intelligent information to be utilized to perform the assistance based on the identifying data, and the like.

5 Claims, 6 Drawing Sheets

SYSTEM AND METHOD FOR PROMOTING UTILIZATION OF MEDICAL INFORMATION

BACKGROUND OF THE INVENTION

1. Field of the Invention

The present invention is related to a system and method for promoting utilization of intelligent information, obtained from medical images.

2. Description of the Related Art

Accompanying technical advancements in medical imaging apparatuses, it has become comparatively easy to obtain image data (volume data) that represent the anatomical structures of humans three dimensionally. Conventionally, volume data had been obtained by obtaining a plurality of tomographic images (two dimensional image data) with an imaging apparatus, then reconstructing the tomographic images with an image processing apparatus. Recently, imaging apparatuses which are capable of directly outputting volume data are becoming mainstream. Particularly, the time required to perform CT (Computed Tomography) examinations has been greatly reduced, due to the use of multiple detectors and the introduction of high speed imaging methods, and the number of CT examinations which are performed daily is increasing.

However, processes for analyzing volume data requires long amounts of time, because they include more data than two dimensional data. For this reason, the number of cases that can be analyzed daily is decreasing. That is, presently, analysis cannot keep up with the increased number of examinations.

In order to ameliorate these circumstances, U.S. Patent Application Publication No. 20070237380 proposes providing a preliminary processing apparatus separately from an apparatus employed in diagnostic observation of medical images. The preliminary processing apparatus determines the purpose of examination and the imaged region, by utilizing instruction data from a system that instructed examination. Then, the preliminary processing apparatus administers image processes onto image data obtained by the examination, based on the determined information. At this time, various image processing parameters which have been extracted or determined during the image processing step are saved in a database. This method enables physicians to administer image processes onto the image data obtained by the examination, using the parameters which are saved in the database, to shorten the amount of time required to analyze the image data.

In conventional hospitals, people who utilized examination results were limited to physicians who ordered examinations. Accordingly, the method of U.S. Patent Application Publication No. 20070237380 that executes preliminary processes according to the purposes of examination and instructions ordered by individual physicians is effective in improving processing efficiency.

However, if data processing systems that enable data sharing within hospitals are built, it is expected that opportunities for data obtained with a specific purpose to be utilized for a different purpose will increase. For example, abdominal CT data obtained by an examination performed in the internal medicine department of a hospital may be employed by a surgeon for a laparotomy simulation. As another example, abdominal CT data obtained by an examination of the stomach in the internal medicine department may be employed in fat distribution evaluation (to prevent adult onset lifestyle related diseases). In an environment in which departments of hospitals and physicians share data, it is cot favorable for preliminary processes to be administered onto data according to the purposes of examination. This is because in the case that the data are employed for a different purpose, a long amount of time will be required to perform adjustments, which will result in a deterioration in processing efficiency.

SUMMARY OF THE INVENTION

The objective of the present invention is to solve the aforementioned problem, by collecting data (medical information) suitable for general use at hospitals, and by providing an environment that facilitates utilization of the collected medical information.

A system of the present invention realizes the objective of promoting utilization of medical information, by being equipped with a region judging means, an intelligent information generating means, an intelligent information generation instructing means, an intelligent information registering means, and a work assisting means, to be described below.

The region judging means obtains an image to which first attached data is attached by a medical imaging apparatus, and judges a region (the head region, the thoracic region, the abdominal region, etc.) represented by the image by image analysis or by referring to the first attached data. Note that the image may be two dimensional image data or three dimensional image data.

The intelligent information generating means, generates at least one piece of intelligent information related to at least one body tissue (organs, bones, blood vessels, etc.), which is included in the obtained image, by extracting the at least one body tissue or analyzing the at least one body tissue, and outputs the at least one piece of intelligent information. The body tissues included in the image differs according to the region represented by the image. In addition, because the methods for extraction and analysis differs according to the type of body tissue, a plurality of intelligent information generating means are provided.

Note that in the present specification, knowledge that can be obtained either directly or indirectly from images is referred to as "intelligent information". For example, if a cardiac region is extracted from an image, knowledge related to the shape of the heart can be obtained. Accordingly, a cardiac region image is a piece of intelligent information. In addition, various values obtained by analyzing the cardiac region are also pieces of intelligent information.

The intelligent information generation instructing means estimates at least one body tissue included in the image based on the judgment results of the region judging means, and instructs the intelligent information generating means that performs one of extraction and analysis of the at least one estimated body tissue to generate the intelligent information. For example, in the case that the region is the thorax, instructions are output to the intelligent information generating means that extracts the heart and to the intelligent information generating means that extracts lungs, etc., and in the case that the region is the abdomen, instructions are output to the intelligent information generating means that extracts the stomach and the intelligent information generating means that extracts the liver, etc.

The intelligent information registering means, attaches second attached data to the intelligent information, which has been generated by each of the intelligent information generating means based on instructions from the intelligent information generation instructing means, correlates the pieces of intelligent information to which the second attached data are attached with the image to which the first data is attached, and registers the correlated intelligent information in a database. That is, a common piece of attached data (header) is attached to the pieces of intelligent information, which are output from each of the intelligent information generating means in different formats, to normalize the intelligent information prior to storage thereof.

The work assisting means executes assisting processes that assist the work of medical workers by utilizing the intelligent information registered in the database. Here, medical workers include radiation technicians and the like, in addition to physicians. In addition, examples of the work to be assisted include: diagnosis; surgery; treatment; and research.

The work assisting means also executes filtering processes that obtain identifying data of the medical workers who perform the work, and limit the range of assistance or the range of intelligent information to be utilized to perform the assistance based on the identifying data. The filtering processes may limit both the range of assistance and the range of intelligent information.

In the system configured as described above, the work assisting means may generate new pieces of intelligent information during the assisting process that assists the work of the medical workers. In this case, the intelligent information registering means attaches the second attached data to the new pieces of intelligent information generated by the work assisting means, and registers the pieces of intelligent information to which the second attached data are attached in the database. For example, knowledge which is obtained as a result of referring to a plurality of pieces of intelligent information during the course of diagnosis may be registered as a new piece of intelligent information. Alternatively, a piece of intelligent information which has already been registered may be updated, based on newly obtained knowledge.

The work assisting means may limit (narrow) the range of assistance or the range of intelligent information, based on the image that the intelligent information is correlated to. Alternatively, the work assisting means may narrow these ranges by utilizing the second attached data which are attached to the intelligent information. For example, subject (patient) identifying data may be included in the second attached data, and the ranges may be restricted based on the subject identifying data. In this case, the work assisting means is enabled to utilize all pieces of intelligent information which have been generated for the subject, including those which were generated during past examinations. Alternatively, data that identifies at least one of the region, the body tissue, and a disease name may be included in the second attached data, and the ranges may be restricted based on the data that identifies at least one of the region, the body tissue, and the disease name. In this case, the work assisting means is enabled to utilize all pieces of intelligent information which have been generated for the region (or the body tissue, or the disease name) which have been generated up to present.

The intelligent information registering means may not only register the generated pieces of intelligent information as individual sets of data, but may register collective objects that includes a plurality of pieces of intelligent information in the database. For example, a collective object that includes all pieces of intelligent information generated from a single image, or a collective object that includes all pieces of intelligent information having common values in the second attached data may be generated and registered in the database. Thereby, all pieces of intelligent information obtained during a single examination, all pieces of intelligent information obtained regarding a single patient, all pieces of intelligent information obtained regarding a specific disease, and the like, may be saved as individual data objects, which facilitates data management.

Note that examples of the processes by which the intelligent information generating means generates the pieces of intelligent information include: body surface extraction; cranial extraction; lung field extraction; bronchial tube extraction; cardiac extraction; thoracic bone extraction; coronary artery extraction; left ventricle extraction; abdominal bone extraction; liver extraction; hepatic vessel extraction; abdominal fat extraction; abnormal pattern detection; cardiac function analysis; blood vessel shape analysis; bone shape analysis; bone motor analysis; and fat distribution evaluation. In addition, examples of the assisting processes executed by the work assisting means include processes that assists: diagnosis; surgery; treatment; and research.

A method of the present invention is a method for promoting utilization of medical information, by operating the system described above. In this method, (A) upon imaging by a medical imaging apparatus, at least one computer executes the processes of: (a1) obtaining an image, to which first attached data is attached by the medical imaging apparatus; (a2) judging a region represented by the image by performing one of: image analysis and referring to the first attached data; (a3) estimating at least one body tissue included in the image based on the judgment results regarding the represented region; (a4) generating at least one piece of intelligent information related to the estimated body tissue, by performing one of extraction of the estimated body tissue and analysis of the estimated body tissue; and (a5) attaching second attached data to the intelligent information, correlating the pieces of intelligent information to which the second attached data are attached with the image to which the first data is attached, and registering the correlated intelligent information in a database; and (B) upon work being performed by medical workers, at least one computer executing: (b1) assisting processes that assist the work of medical workers by utilizing the intelligent information registered in the database; and (b2) filtering processes that obtain identifying data of the medical workers who perform the work, and limit at least one of the range of assistance and the range of intelligent information to be utilized to perform the assistance based on the identifying data.

According to the present invention, pieces of intelligent information included in an image are automatically and thoroughly collected by the system. Therefore, a large burden is not placed on medical workers with regard to data collection. In addition, the pieces of intelligent information are generated based only on the image and the data attached thereto by an imaging apparatus. Therefore, the pieces of information are suited for general use, that is, suited for use by arbitrary users for desired purposes. Meanwhile, in the assistance of work that utilizes the accumulated pieces of intelligent information, usable functions and usable information are limited by data that identifies medical workers. Therefore, the medical workers can perform their duties efficiently, without being distracted by unnecessary functions and unnecessary information.

DESCRIPTION OF THE PREFERRED EMBODIMENTS

Hereinafter, a system and a method of the present invention will be described with reference to the attached drawings. First, processes which are administered onto medical images obtained by imaging, and the utilization states of the process results will be described, in order to clarify the objective and advantageous effects of the present invention.

Figure 1:
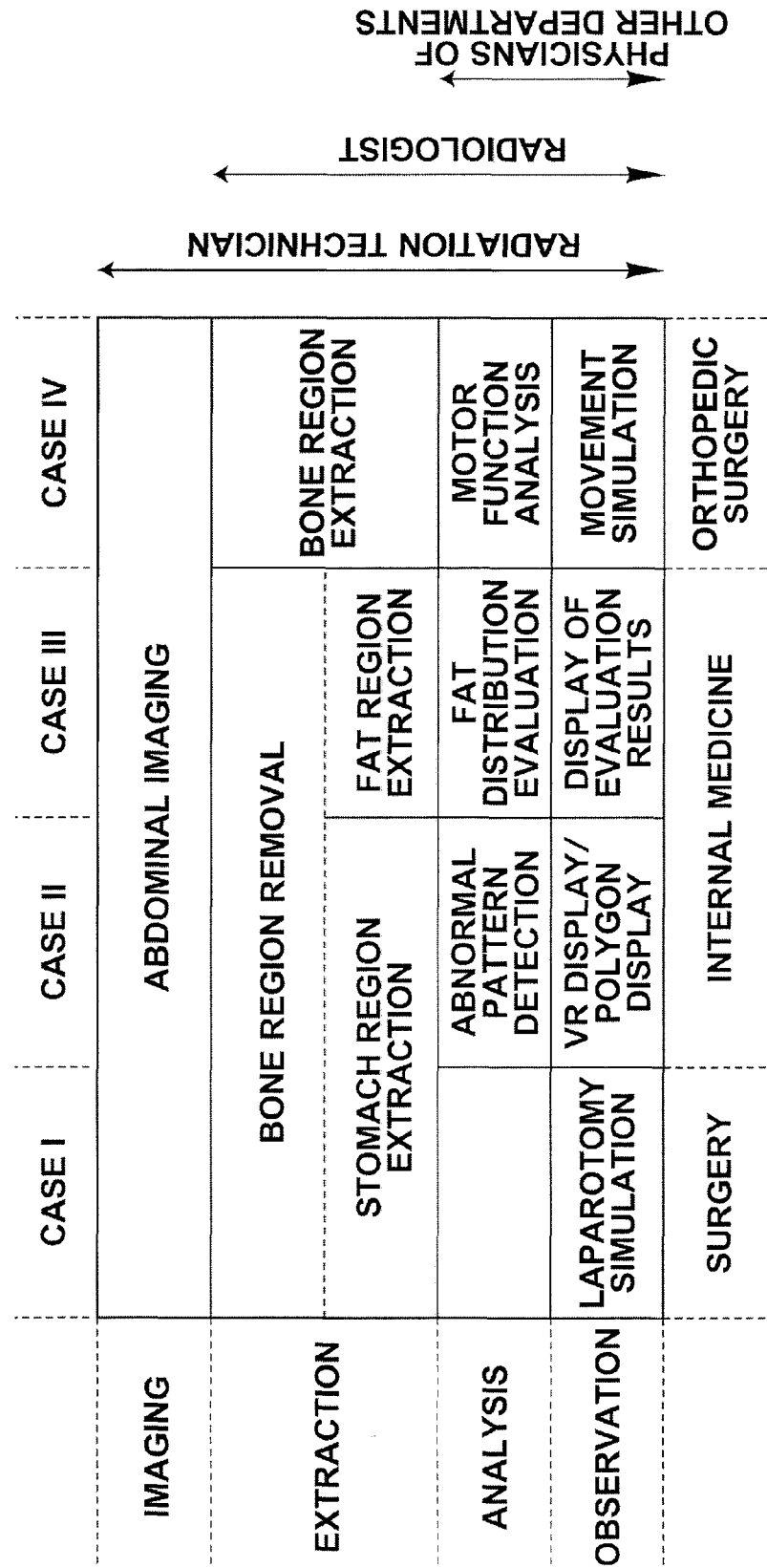
FIG. 1 is a diagram that illustrates processes which are administered onto a medical image for different phases and for different purposes of examination (in the case of an image of the abdomen).

Commonly, processes related to medical images can be broadly classified into the four phases of: imaging; extraction; analysis; and assistance. FIG. 1 is a diagram in which processes, which are executed with an image of the abdomen as the target of processing, are classified according to phases and purposes of examination. As illustrated in FIG. 1, a radiation technician is generally involved in all four phases. A radiologist is generally involved in the extraction, analysis, and assistance phases. Meanwhile, physicians of other departments are commonly only involved in the analysis and assistance phases.

For example, in the case that a surgeon orders imaging of the abdomen to perform simulation of a stomach laparotomy (Case I), bone region removal and stomach region extraction are performed in the extraction phase, and a laparotomy simulation is executed with volume data that represents the stomach region in the assistance phase. As another example, in the case that an internist orders imaging of the abdomen to study the condition of the stomach (Case II), bone region removal and stomach region extraction are performed in the extraction phase, and abnormal pattern detection is performed in the analysis phase, utilizing volume data that represents only the stomach region obtained in the extraction phase. Thereafter, the detection results of abnormal pattern detection obtained in the analysis phase are displayed as VR (Volume Rendering) display, or as polygon display in the assistance phase.

On the other hand, in the case that the internist orders imaging, but the purpose of the imaging is to evaluate fat distribution (Case III), bone region removal and fat region extraction are performed in the extraction phase, fat distribution is evaluated in the analysis phase, and the evaluation results are displayed in the assistance phase. In addition, in the case that an orthopedic surgeon orders imaging of the abdominal area to perform movement simulation of bones in the waist area (Case IV), bone region extraction is performed in the extraction phase, motor analysis is performed in the analysis phase, and the movement simulation that utilizes the motor analysis results is performed in the assistance phase.

There are several processes which are executed in common among the plurality of types of examinations, such as the bone region removal and the stomach region extraction indicated in the examples of FIG. 1. However, the types and the processing conditions of the processes which are executed during each phase are generally determined based on physicians' orders and wishes, or based on the purposes of examination. For this reason, even if the subject of examination in each of Cases I through IV is a single patient, and abdominal imaging is performed only once, the bone region removal and the stomach region extraction are normally performed separately for each case. In addition, the data generated during the extraction phase and the analysis phase are often used only once.

However, pieces of medical information which are generated during the extraction phase and the analysis phase include many items of knowledge, and such knowledge must have utilization value in other processes. In addition, reutilization of previously obtained knowledge is preferable from the viewpoints of work efficiency and costs. However, accumulating obtained knowledge in a random manner will not promote utilization of medical information. In order to promote utilization of medical information, first, a mechanism that enables sharing of a large amount of medical information that can be utilized in various processes in an easy manner is necessary. Second, a mechanism that enables utilization of the large amount of accumulated medical information in an organized manner is necessary. Hereinafter, an example of a system equipped with these mechanisms will be described.

Figure 2:
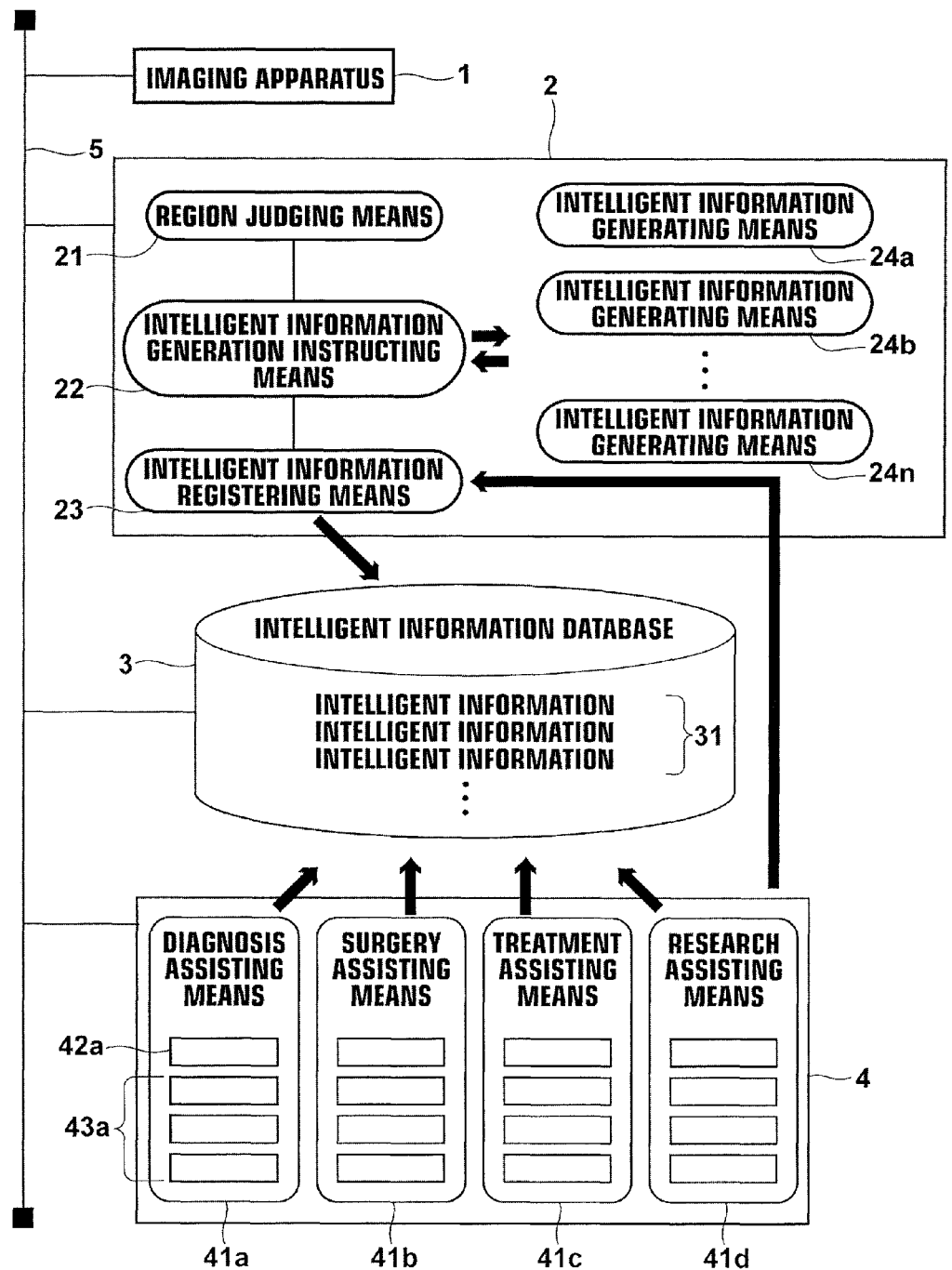
FIG. 2 is a diagram that illustrates the schematic structure of a system for promoting utilization of medical information according to an embodiment of the present invention.

FIG. 2 is a diagram that illustrates the schematic structure of a system for promoting utilization of medical information according to an embodiment of the present invention. As illustrated in FIG. 2, the system is equipped with: an imaging apparatus 1 (modality); a server computer 2; an intelligent information database 3; and a workstation 4. Each component is connected to each other so as to be capable of communications via a network 5. For the sake of simplifying the description, FIG. 2 illustrates an example in which only one of each component is provided. However, a plurality of different types of imaging apparatuses are connected to the network 5 as the imaging apparatus 1. In addition, a plurality of workstations 4 are provided, according to the number of medical workers, such as radiation technicians, radiologists, and physicians in each department of a hospital.

In the present embodiment, the network 5 is a local area network that connects various apparatuses within the hospital. However, in the case that the workstation 4 is provided in a different hospital or in a clinic, the network 5 may be of a configuration in which the local area networks of the hospitals are connected via the Internet or via dedicated telecommunication lines. In either case, it is desirable for the network 5 to be that which can realize high speed transmission of image data, such as an optical network.

The imaging apparatus 1 is an apparatus that generates two dimensional or three dimensional image data (images) by imaging subjects, attaches data (first attached data) defined by DICOM standards to the image data, and outputs the image data. The attached data includes at least identifiers of the subject, identifiers of the examination, and identifiers of each image. The imaging apparatus 1 may be an imaging apparatus of the type that performs all of the processes from imaging of the subject to generation of image data, or may be an imaging apparatus of the type in which an apparatus that records images onto recording sheets is provided separately from a readout apparatus that reads out images form the recording sheets to generate image data. Specific examples of the imaging apparatus 1 include: a CT (Computed Tomography) apparatus; an MR (Magnetic Resonance) apparatus; an X ray imaging apparatus; a PET (Positron Emission Tomography) apparatus, and an ultrasound imaging apparatus.

The server computer 2 is a general use computer having a comparatively high processing performance, in which a programs that define a region judging process, an intelligent information generation instructing process, an intelligent information registering process, and an intelligent information generating process, are installed. These programs are distributed by being recorded in storage media such as CD-ROM's and DUD's, and installed in the server computer 2 from the storage media. Alternatively, the programs may be recorded in a storage unit attached to a different computer in a state in which it is accessible from the exterior, or recorded in network storage in a state in which it is accessible from the exterior, and downloaded to and installed in the server computer 2 as necessary. Thereby, the server computer 2 functions as a region judging means 21, an intelligent information generation instructing means 22, an intelligent information registering means 23, and intelligent information generating means 24a, 24b, ... 24n.

The intelligent information database 3 is constituted by a high capacity storage and a general use computer having a comparatively high processing performance. A software program that provides the functions of a DBMS (Database Management Server) is built in to the computer. The DBMS saves pieces of intelligent information, for which registration is requested by the intelligent information registering means 23 of the server computer 2, in the high capacity storage. In addition, the DBMS extracts and provides pieces of intelligent information that fits search criteria, when requests to refer to registered pieces of intelligent information are received. Note that the storage is not limited to that which is connected to the computer that functions as the DBMS, and may be an NAS (Network Attached Storage) or an SAN (Storage Area Network) which is directly connected to the network 5.

The workstation 4 is constituted by a general use processing apparatus (computer), one or two high resolution displays, and input devices, such as a keyboard and a mouse. Work assisting programs that define processes for assisting each work operation to be performed by medical workers, and filtering programs for limiting the functions realized by executing the work assisting programs are installed in the processing apparatus. These programs are distributed by being recorded in storage media such as CD-ROM's and DVD's, and installed in the workstation 4 from the storage media. Alternatively, the programs may be recorded in a storage unit attached to a different computer in a state in which it is accessible from the exterior, or recorded in network storage in a state in which it is accessible from the exterior, and downloaded to and installed in the workstation 4 as necessary. Thereby, the workstation 4 functions as assisting means 41a through 41d that assist each work operation.

The processes which are executed by the server computer 2 will be described, with continued reference to FIG. 2. The region judging means 21 judges what region is represented by the images. As described previously, the data (first attached data) as defined by the DICOM standard are attached to the image data output from the imaging apparatus in the present embodiment. The attached data normally includes information that specifies the imaging apparatus and the imaged region. Accordingly, the server computer 2 judges the imaged region, by referring to the data attached to received image data.

Alternatively, the imaged region may be judged by directly analyzing the image data. Various methods for judging imaged regions by analyzing image data are known, such as: the template matching method, and classification based on features. A method in which user intervention corrects discrimination results in the case that automatic discrimination does not yield accurate results has also been proposed (refer to U.S. Patent Application Publication No. 20080267481). As a further alternative, the attached data may be referred to as a basic rule, and the imaged region may be judged by performing analysis of image data only in cases that the attached data does not include information regarding the imaged region.

The judgment results output from the region judging means 21 are input to the intelligent information generation instructing means 22. The intelligent information generation instructing means 22 estimates body tissues (organs, blood vessels, bones, etc.) which are included in the images, based on the judgment results. Then, the intelligent information generation instructing means 22 instructs one or more intelligent information generating means that performs extraction or analysis of the estimated body tissue to generate intelligent information related to the body tissue.

In the present embodiment, programs that execute: body surface extraction; cranial extraction; lung field extraction; bronchial tube extraction; cardiac extraction; thoracic bone extraction; coronary artery extraction; left ventricle extraction; abdominal bone extraction; liver extraction; hepatic vessel extraction; abdominal fat extraction; abnormal pattern detection; cardiac function analysis; blood vessel shape analysis; bone shape analysis; bone motor analysis; and fat distribution evaluation, are built into the server computer 2 such that it functions as the intelligent information generating means 24a through 24n. However, these functions are merely examples, and it goes without saying that only a portion of these functions, or other functions may be built into the server computer 2.

The intelligent information generation instructing means 22 selects means for executing processes related to the estimated region from among the intelligent information generating means 24a through 24n, and causes them to operate. For example, in the case that the judged image region is the thorax, the heart, lungs, ribs, coronary arteries, and other blood vessels are present in the thorax. Accordingly, the thoracic bone extraction program, the cardiac extraction program, the coronary artery extraction program, the left ventricle extraction program, and the blood vessel shape analyzing program are executed, in order to gain knowledge about the shapes and functions of the heart, the lungs, the ribs, and the blood vessels.

When the processes performed by each of the extraction programs and the analysis program are completed, the intelligent information generation instructing means 22 supplies the processing results of the programs to the intelligent information registering means 23. The intelligent information registering means 23 attaches identifying data of the images (image identifier, date of obtainment, imaging apparatus, imaged region, etc.) and identifying data of the subject (patient) to the generated pieces of intelligent information as attached data (second attached data), then registers the pieces of intelligent information in the intelligent information database 3. By including the two pieces of identifying data in the attached data, the image and the pieces of intelligent information, the image region and the pieces of intelligent information, and the patient and the pieces of intelligent information are correlated with each other. The attached data are referred to in the filtering process, to be described later.

In addition, generation conditions of pieces of intelligent information are also attached to the pieces of generated intelligent information as attached data. The generation conditions of the pieces of intelligent information are represented in the format "Processing Content_Object of Processing (body tissue)". "Extraction" and "Labeling" are two contents of processing in the extraction phase, and "Analysis" and "Detection" are two contents of processing in the analysis phase. For example, the extraction result of a heart is labeled "EXTRACT_HEART". By including the generation conditions of the pieces of intelligent information, body tissues and the pieces of intelligent information are correlated. These attached data are also referred to in the filtering process, to be described later.

Figure 3:
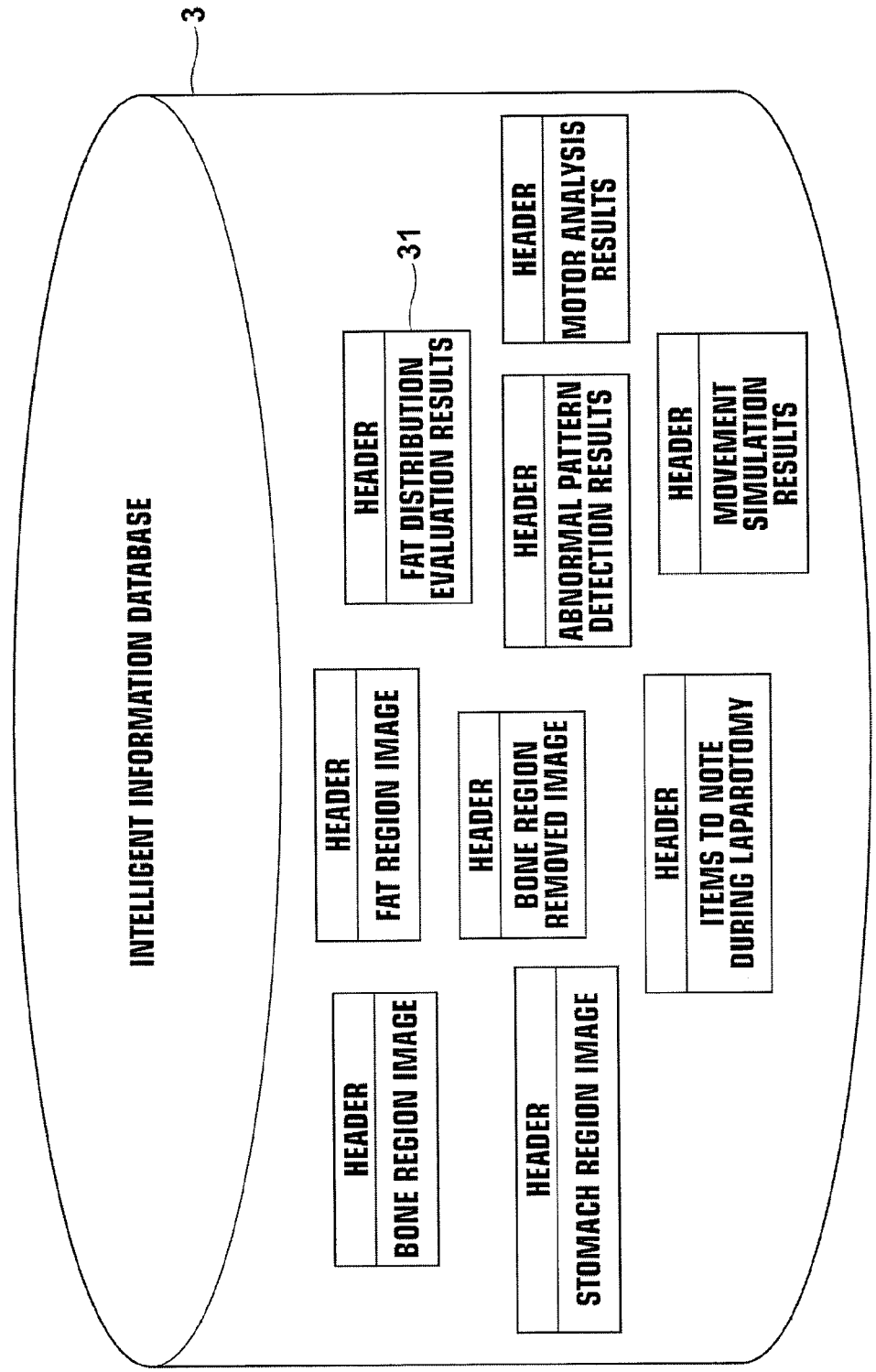
FIG. 3 is a diagram that illustrates examples of pieces of intelligent information which are registered in an intelligent information database.
Figure 4:
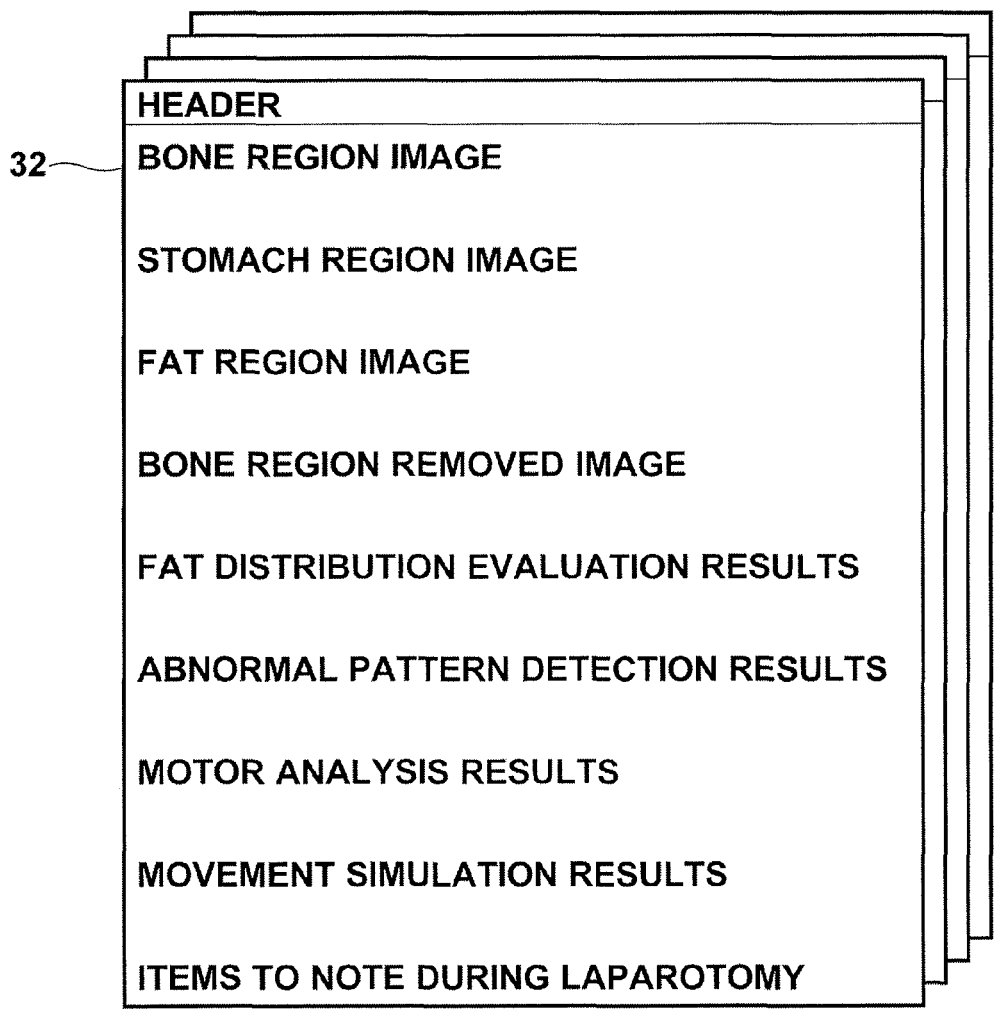
FIG. 4 is a diagram that illustrates an example of pieces of intelligent information which are registered as a collective object.

Next, the characteristics and the advantageous points of the intelligent information database 3 will be described. FIG. 3 is a diagram corresponding to FIG. 1 that illustrates examples of pieces of intelligent information which are registered in an intelligent information database. The pieces of intelligent information are managed as XML data or SGML data, for example. Pieces of intelligent information which are generated in the extraction phase, the analysis phase, and the assistance phase are all registered in the intelligent information database 3 as data 31 in the same format. That is, the data 31 are constituted by header regions of a common format and storage regions for storing the pieces of intelligent information. The pieces of intelligent information are stored in the storage regions, and the aforementioned attached data (second attached data) are stored in the header regions. In addition, pieces of intelligent information to be utilized by surgeons, pieces of intelligent information to be utilized by internists, pieces of intelligent information to be utilized by orthopedic surgeons, and pieces of intelligent information to be utilized by radiation technicians are all registered in the intelligent information database 3 as data 31 of the same format, without any distinctions. The results of examinations, and image data and analysis results when no abnormalities were found are also registered as data of the same format.

Registration of medical information in databases is conventional. For example, storing images output from a plurality of imaging apparatuses in a single location has been performed for a long time. Recently, building of similar case databases that store images in which similar patterns have been detected has also been proposed. However, the objectives of conventional databases are to organize pieces of medical information, which are obtained at the same phase and are utilized later for the same purpose, and to store these pieces of medical information at a single location. For this reason, pieces of medical information which are to be utilized for a specific purpose had been efficiently stored and utilized. However, pieces of medical information which are not utilized for the specific purpose were not registered in databases, and it had been necessary to search for such pieces of medical information via alternate routes.

In contrast, the intelligent information database 3 stores all types of pieces of intelligent information which are included in images in the same format, regardless of the phase in which they are obtained, the method by which they are generated, their planned use, and the purpose of their use, as illustrated in FIG. 3. That is, the intelligent information database 3 stores all types of pieces of intelligent information in a normalized manner. Thereby, the intelligent information database 3 is a collection of all of the pieces of intelligent information which are generated based on each of the images, in other words, all of the knowledge at the hospital.

When registering the pieces of intelligent information, the pieces of intelligent information may be registered in units of pieces of intelligent information, to which the attached data (headers) are attached, output by each of the intelligent information generating means 24. Alternatively, collective objects 32 that include all pieces of intelligent information generated from individual images may be generated, and registration may be performed in units of the collective objects. In the latter method, the pieces of intelligent information obtained during a single examination are collected into one collective object, which facilitates storage and maintenance of data.

In addition, pieces of intelligent information that include common values in the header regions (within the second attached data) thereof may be selected, and collective objects that include all of the selected pieces of intelligent information may be generated and registered. If all pieces of intelligent information that have subject identifying data in common are registered as a single collective object, all of the knowledge regarding the subject, including knowledge which had been obtained in the past, may be referred to, simply by obtaining the collective object. Similarly, pieces of intelligent information having common imaged regions, common body tissues, and common disease names may be selected and registered as collective objects. In this case, various types of knowledge regarding the imaged regions, the body tissues, and disease names, simply by obtaining these collective objects.

Next, the configuration of the workstation 4 will be described in greater detail, with reference to FIG. 2. The work station 4 is equipped with work assisting means, for reading out the pieces of intelligent information from the intelligent information database 3 and utilizing the pieces of intelligent information to assist the work of medical workers (physicians, radiation technicians, etc.) FIG. 2 illustrates a diagnosis assisting means 41a, a surgery assisting means 41b, a treatment assisting means 41c, and a research assisting means 41d as examples of the work assisting means.

The diagnosis assisting means 41a is constituted by a filtering program 42a that executes a filtering process, and a plurality of assistance processing programs 43a that provide various types of assisting functions. The surgery assisting means 41b, the treatment assisting means 41c, and the research assisting means 41d are also each constituted by a filtering program and one or more assistance processing programs.

The assistance processing programs of the diagnosis assisting means 41a provide the functions of: displaying diagnostic images (either singly or displayed with comparative images); visualization and display of organ functions; notification of detected abnormalities; and provision of information regarding similar cases, for example. The assistance processing program of the surgery assisting means 41b provides a surgery simulation function, for example. The assistance processing programs of the treatment assisting means 41c provide the functions of: listing treatment protocols based on similar cases; and movable range simulations of bones and muscles, for example. The assistance processing program of the research assisting means 41d provides a statistical analysis function with the data accumulated in the intelligent information database 3 as the objects of analysis.

The diagnosis assisting means 41a, the surgery assisting means 41b, the treatment assisting means 41c, and the research assisting means 41d determine the functions to be provided, that is, the assisting processes to be administered (range of assistance) for each user that utilizes the work station, and causes programs that provide functions within the determined range to be executed. Because programs that provide functions other than those within the range are not executed, the functions outside the range do not appear on a display screen.

Figure 5:
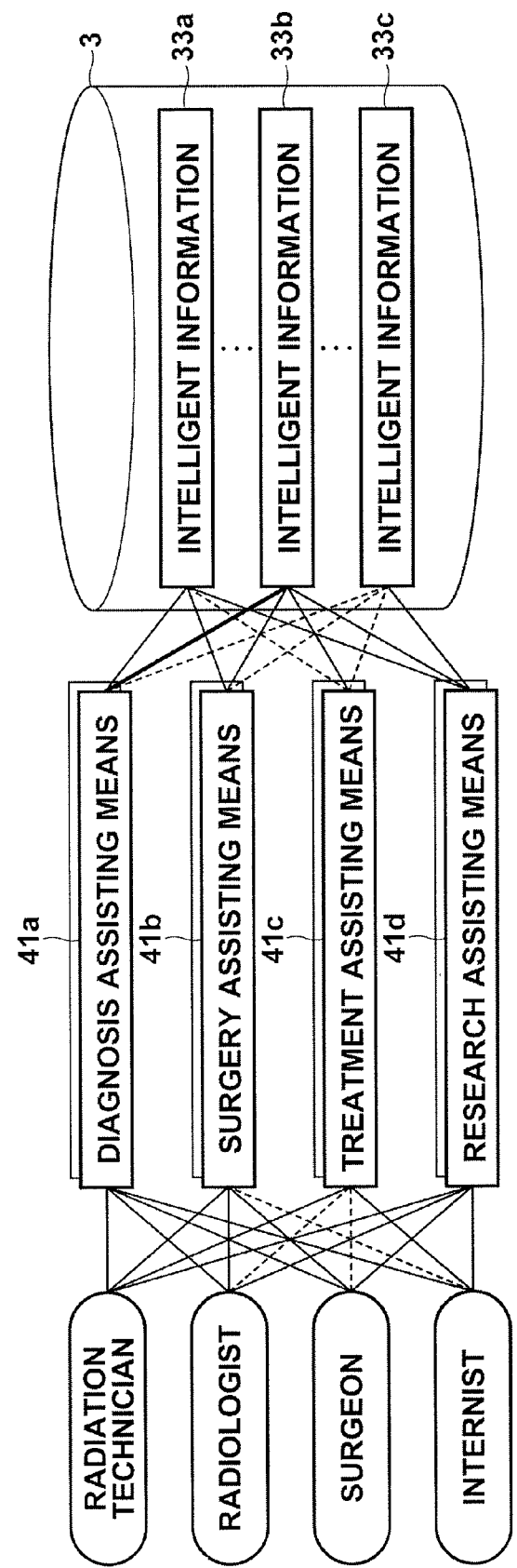
FIG. 5 is a diagram for explaining limitations of ranges of assistance and ranges of usable intelligent information.

FIG. 5 is a diagram for explaining the limitations of ranges of assistance and ranges of usable intelligent information, and illustrates the relationships among users, the work assisting means, and pieces of intelligent information. In FIG. 5, the solid lines indicate usable relationships (no restrictions on utilization), the broken lines indicate unusable relationships (restriction of utilization), and the bold lines indicate relationships in which the usability depends on the user. As illustrated in FIG. 5, a portion of the users (for example, the radiation technician) is enabled to utilize all of the functions provided by the diagnosis assisting means 41a, the surgery assisting means 41b, the treatment assisting means 41c, and the research assisting means 41d. However, the other users are limited in the functions that they are enabled to utilize. For example, because functions such as surgical simulation are generally unnecessary for internists, the workstation 4 restricts execution of the surgery assisting means 41b in the case that the user is an internist.

In addition, each of the diagnosis assisting means 41a, the surgery assisting means 41b, the treatment assisting means 41c, and the research assisting means 41d is constituted by a single filtering program and the plurality of assistance processing programs that provide various assisting functions, as described previously. The execution of the assistance processing programs is restricted according to the results of the filtering processes.

Figure 6:
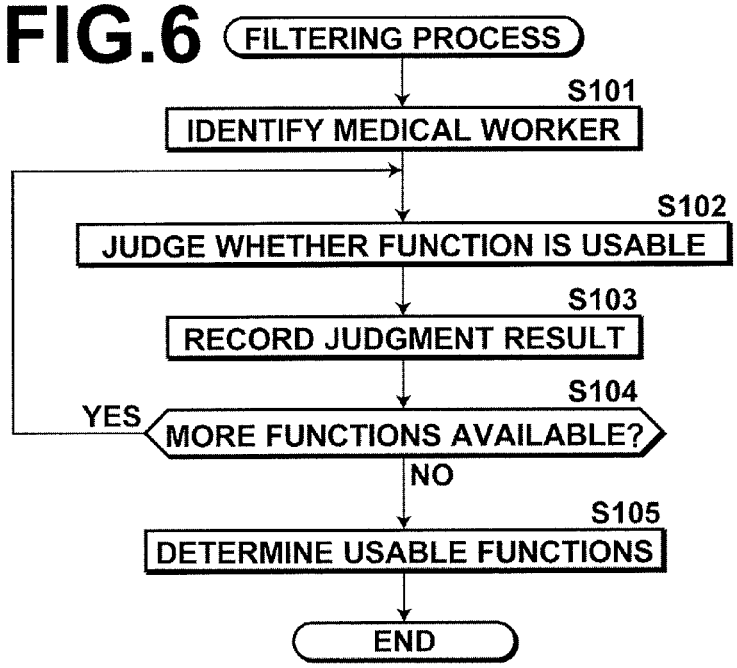
FIG. 6 is a flow chart that illustrates the steps of a filtering process executed by a work assisting means.

FIG. 6 is a flow chart that illustrates the steps of a filtering process executed by a work assisting means. The work assisting means judges the identity of a medical worker who is operating the workstation 4 (step S101). In the present embodiment, the login ID which is input by the user when they log in to the workstation 4 is obtained as identifying data of the medical worker, and the identity of the medical worker is judged based on this identifying data.

Next, whether a function provided by the work assisting means is usable by the user is judged based on the judgment results of the user (step S102). This judgment is performed based on correlations among medical workers and assisting functions (or body tissues), which are set in advance. The judgment results are recorded in a memory or the like (step S103). In the case that the work assisting means provides a plurality of functions, the processes of steps S102 and S103 are repeated (step S104). For example, in the filtering process executed by the diagnosis assisting means 41a, whether the user is enabled to utilize diagnosis assisting functions for subjects of diagnosis, such as a heart diagnosis assisting function, a liver diagnosis assisting function, and a bone diagnosis assisting function is judged for each subject of diagnosis. Thereby, the functions that a medical worker who wishes to utilize the assisting functions is enabled to utilize are determined (step S105). That is, the range of assistance executed by the work assisting means is determined.

Programs for executing processes to realize the functions which have been judged to be usable are loaded into the memory. The work assisting means displays user interfaces and receives operational input only for the assisting functions which have been judged to be available for use by the user.

Figure 7:
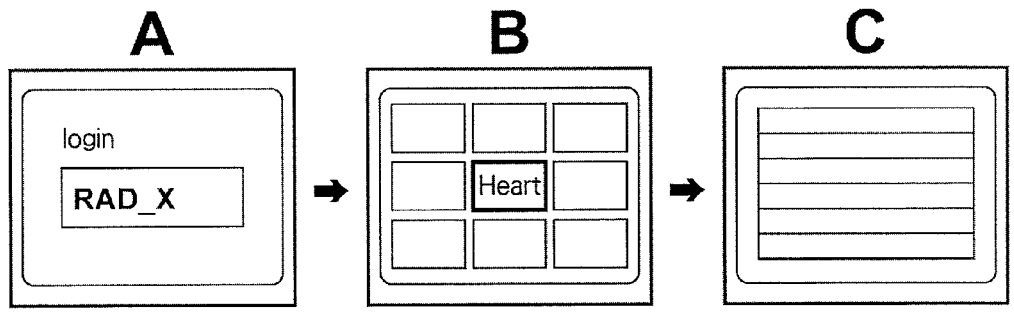
FIG. 7 is a diagram that illustrates the relationship between a user and a display screen (in the case that the user is a radiation technician).
Figure 8:
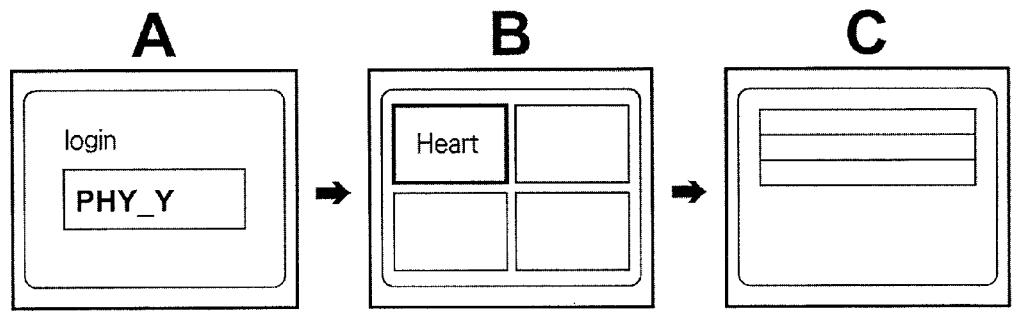
FIG. 8 is a diagram that illustrates the relationship between a user and a display screen (in the case that the user is an internist).

For example, in the case that a login ID indicating that a user is a radiation technician or a radiologist is input as illustrated in A of FIG. 7, it is judged that all of the functions provided by the work assisting means are necessary. Therefore, selection buttons for all functions are displayed, as illustrated in B of FIG. 7. On the other hand, in the case that a login ID indicating that a user is an internist is input as illustrated in A of FIG. 8, only selection buttons for work assisting functions related to organs and blood vessels are displayed, and selection buttons for other functions are not displayed on the display screen.

In addition, in the case that the user selects the diagnosis assisting function for the heart in the display screen illustrated in B of FIG. 7, a list of cardiac region images which are registered in the intelligent information database 3 as intelligent information is displayed, as illustrated in C of FIG. 7. On the other hand, in the case that the diagnosis assisting function for the heart is selected in the display screen illustrated in B of FIG. 8, that is, in the case that the user is an internist, a list of cardiac region images only of the internist's own patients is displayed, as illustrated in C of FIG. 8.

The work assisting programs which are executed in this restricted manner perform processes utilizing the intelligent information registered in the intelligent information database 3. At this time, the range of intelligent information which is available for use by the work assisting programs is limited by the user who is using the workstation 4. For example, in the example of FIG. 5, the diagnosis assisting means 41a is caused to operate in the case that the user is one of a radiation technician, a radiologist, a surgeon, and an internist. In addition, the diagnosis assisting means 41a utilizes intelligent information 33a for the processes executed thereby, regardless of the user. However, use of intelligent information 33b is restricted according to the user. The intelligent information 33b is utilized in the case that the user is a surgeon, but not utilized in the case that the user is a technician or a physician from a department other than surgery.

Additional registration and updating of intelligent information will be described with reference to FIG. 2. The aforementioned pieces of intelligent information are automatically generated from a single image by the intelligent information generating means. Pieces of intelligent information which are generated during the process of work assistance are also pieces of intelligent information which are to be registered in the intelligent information database 3. There are cases that new knowledge is gained based on a plurality of images and a plurality of pieces of intelligent information correlated therewith during the course of diagnosis and research.

For example, in the case that a patient undergoes examinations in a plurality of departments of the hospital, a plurality of images that represent different regions of the same patient are obtained, and pieces of intelligent information are generated from each of the images. In this case, physicians can organize and confirm all of the pieces of intelligent information related to this patient, and may notice correlations among diseases which have been detected in different regions, as a result of confirming pieces of intelligent information regarding the patient's entire body. In this case, the work assisting means correlates pieces of intelligent information that indicates the correlation among the diseases (by attaching second attached data), and registers the pieces of intelligent information in the intelligent information database 3. This registration process is executed based on user input.

In addition, in the case that pieces of intelligent information related to a plurality of patients having the same disease are registered, statistical analysis may be performed with respect to the pieces of intelligent information. Thereby, knowledge which is helpful in preventing disease, such as a relationship between occlusion of the coronary artery and myocardial infarction, may be obtained. In these cases, the work assisting means correlates this knowledge with a disease name (by attaching second attached data), and registers the knowledge in the intelligent information database 3. This registration process is executed based on user input as well.

Meanwhile, there are cases in which it becomes necessary to update pieces of intelligent information during the course of work assistance utilizing the automatically generated pieces of intelligent information. For example, because region extracting processes cannot always extract regions accurately, there are cases in which region images having low image quality are registered. In these cases, region images extracted from past images of the same patient are referred to correct the outline of the region, and the corrected image is reregistered, to update the piece of intelligent information.

In addition, in cases that region images are utilized for comparative image diagnosis, it is necessary to employ a uniform positional coordinate system among the images. The process to uniformize the coordinate systems may be executed immediately after the region images are generated by the intelligent information generating means, or executed by the work assisting means when a comparative image diagnosis screen is displayed. In both cases, the registered region images are replaced with corrected region images represented with the uniform coordinate system, by an intelligent information updating process.

According to the system of the present embodiment, regions represented by images are automatically judged simply by transmitting the images which are obtained during examinations from the imaging apparatus 1 to the server computer 2, and processes for obtaining knowledge related to organs, bones, blood vessels and the like included in the regions are automatically executed. Thereby, all pieces of intelligent information which are included in the images can be thoroughly and simply collected, without placing a large burden on users. In addition, the system of the present embodiment enables pieces of intelligent information which are newly obtained during the course of work assistance to be registered in the database, and also enables updating of pieces of intelligent information which are already registered in the database. That is, insufficiencies and defects of the automatic process can be compensated for, and the quality of the registered pieces of intelligent information can be improved.

The pieces of intelligent information, which are registered in the database of the system of the present embodiment, are registered as data for general use. Therefore, the pieces of intelligent information can be referred to and utilized by different work assisting means. In addition, because referring to different types of intelligent information simultaneously is facilitated, new knowledge, such as confirmation of diseases in the entire body and correlations among diseases and symptoms, which had been unobtainable with conventional systems, has become easy to obtain.

In the system of the present embodiment, each work assisting means performs the filter processes based on user identifying data. Therefore, even if the types of means for assisting the work of medical workers increase in the future, and even if the types of intelligent information which are registered in the intelligent information database 3 become more varied and increase in number, users will not be distracted by unnecessary display screens or by display of unnecessary information.

Note that the present invention is not limited to the embodiment described above. Various changes and modifications may be added, as long as they do not stray from the spirit and scope of the invention.

What is claimed is:

1. A method for promoting utilization of medical information, comprising:
   (A) upon imaging by a medical imaging apparatus, at least one computer executes the processes of:
   (a1) obtaining an image, to which first attached data is attached by the medical imaging apparatus;
   (a2) judging a region represented by the image by performing analysis of the image and referring to the first attached data;
   (a3) estimating at least one body tissue included in the image based on the judged region;
   (a4) generating at least one piece of intelligent information that is at least one of extraction data and analysis data of the estimated body tissue, by performing one of extraction of the estimated body tissue and analysis of the estimated body tissue; and
   (a5) attaching second attached data to the intelligent information, correlating the pieces of intelligent information to which the second attached data are attached with the image to which the first data is attached, and registering the correlated intelligent information in a database; and
   (B) upon work being performed by medical workers, at least one computer executing:
   (b1) assisting processes that assist the work of medical workers by utilizing the intelligent information registered in the database; and
   (b2) filtering processes that obtain identifying data of the medical workers who perform the work, and limit a range of available assisting processes and a range of intelligent information to be utilized to perform the available assisting processes based on the identifying data and the second attached data,
   wherein:
   data that identifies at least one of the region, the body tissue, and a disease name is included in the second attached data which are attached to the intelligent information;
   the range of assisting processes and the range of intelligent information to be utilized based on the data that identifies at least one of the region, the body tissue, and the disease name is limited,
   the second attached information comprises at least an identity information of the disease name,
   the assisting processes comprise generating new pieces of intelligent information that indicate a correlation among different diseases in diseases corresponding to the identity information of the disease name which is included in the second attached information of the intelligent information to be utilized during the assisting process that assists the work of the medical workers,
   the attaching comprises attaching the second attached data to the generated new pieces of intelligent information, and registering the pieces of intelligent information to which the second attached data are attached in the database, and
   the method further comprising generating one of a collective object that includes all pieces of intelligent information generated from a single image and a collective object that includes all pieces of intelligent information having common values in the second attached data, and registers the generated collective object in the database.

2. A method for promoting utilization of medical information, comprising:
   (A) upon imaging by a medical imaging apparatus, at least one computer executes the processes of:
   (a1) obtaining an image, to which first attached data is attached by the medical imaging apparatus;
   (a2) judging a region represented by the image by performing analysis of the image and referring to the first attached data;
   (a3) estimating at least one body tissue included in the image based on the judged region;
   (a4) generating at least one piece of intelligent information that is at least one of extraction data and analysis data of the estimated body tissue, by performing one of extraction of the estimated body tissue and analysis of the estimated body tissue; and (a5) attaching second attached data to the intelligent information, correlating the pieces of intelligent information to which the second attached data are attached with the image to which the first data is attached, and registering the correlated intelligent information in a database; and
(B) upon work being performed by medical workers, at least one computer executing:
(b1) assisting processes that assist the work of medical workers by utilizing the intelligent information registered in the database; and
(b2) filtering processes that obtain identifying data of the medical workers who perform the work, and limit a range of available assisting processes and a range of intelligent information to be utilized to perform the available assisting processes based on the identifying data and the second attached data,
wherein:
patient identifying data is included in the second attached data which are attached to the intelligent information; and
the range of assisting processes and the range of intelligent information to be utilized based on the patient identifying data included in the second attached data is limited,
the second attached information comprises at least an identity information of a disease name,
the assisting processes comprise generating new pieces of intelligent information that indicate a correlation among different diseases in diseases corresponding to the identity information of the disease name which is included in the second attached information of the intelligent information to be utilized during the assisting process that assists the work of the medical workers;
the attaching comprises attaching the second attached data to the generated new pieces of intelligent information, and registering the pieces of intelligent information to which the second attached data are attached in the database, and
the method further comprises performing a statistical analysis to determine the correlation among the different diseases, the correlation comprising a relationship between occlusion of a coronary artery and myocardial infarction.

3. A system for promoting utilization of medical information, comprising:
region judging unit which obtains an image to which first attached data is attached by a medical imaging apparatus, and which judges a region represented by the image by performing analysis of the image and referring to the first attached data;
a plurality of intelligent information generating units which generate at least one piece of intelligent information that is at least one of extraction data and analysis data body tissue, which is included in the obtained image, by performing one of extraction of the at least one body tissue and analysis of the at least one body tissue;
intelligent information generation instructing unit which estimates at least one body tissue included in the image based on the judged region, and which instructs the intelligent information generating unit that performs one of extraction and analysis of the at least one estimated body tissue to generate the intelligent information;
intelligent information registering unit which attaches second attached data to the intelligent information, which has been generated by each of the intelligent information generating units based on instructions from the intelligent information generation instructing units, for correlating the pieces of intelligent information to which the second attached data are attached with the image to which the first data is attached, and for registering the correlated intelligent information in a database; and
a plurality of work assisting units which execute assisting processes that assist the work of medical workers by utilizing the intelligent information registered in the database; and which filter processes that obtain identifying data of the medical workers who perform the work, and limit a range of available assisting processes and a range of intelligent information to be utilized to perform the assisting processes based on the identifying data and the second attached data,
wherein:
patient identifying data is included in the second attached data which are attached to the intelligent information;
at least one of the work assisting units limits the range of assisting processes and the range of intelligent information to be utilized based on the patient identifying data included in the second attached data,
the second attached data comprises at least an identity information of a disease name used in diagnosing a patient,
the work assisting unit generates new pieces of intelligent information that indicate a correlation among different diseases for diseases corresponding to the identity information of the disease name which is included in the second attached data of the intelligent information to be utilized during the assisting process that assists the work of the medical workers,
the intelligent information registering unit attaches the second attached data to the new pieces of intelligent information generated by the work assisting unit, and registers the pieces of intelligent information to which the second attached data are attached in the database, and
at least one of the plurality of intelligent information generating units, the intelligent information generation instructing unit, and the intelligent information registering unit comprise at least one hardware component,
the work assisting unit further performs a statistical analysis to determine the correlation among the different diseases, the correlation comprising a relationship between occlusion of a coronary artery and myocardial infarction.

4. A system for promoting utilization of medical information, comprising:
region judging unit which obtains an image to which first attached data is attached by a medical imaging apparatus, and which judges a region represented by the image by performing analysis of the image and referring to the first attached data;
a plurality of intelligent information generating unit which generate at least one piece of intelligent information that is at least one of extracted data and analyzed data of body tissue, which is included in the obtained image, by performing one of extraction of the at least one body tissue and analysis of the at least one body tissue;
intelligent information generation instructing unit which estimates at least one body tissue included in the image based on the judged region of the region judging unit, and which instructs the intelligent information generating unit that performs one of extraction and analysis of the at least one estimated body tissue to generate the intelligent information;

intelligent information registering unit which attaches second attached data to the intelligent information, which has been generated by each of the intelligent information generating unit based on instructions from the intelligent information generation instructing unit which correlates the pieces of intelligent information to which the second attached data are attached with the image to which the first data is attached, and which registers the correlated intelligent information in a database; and a plurality of work assisting units which execute: assisting processes that assist the work of medical workers by utilizing the intelligent information registered in the database; and which filters processes that obtain identifying data of the medical workers who perform the work, and limit a range of available assisting processes and a range of intelligent information to be utilized to perform the available assisting processes based on the identifying data and the second attached data, wherein:

data that identifies at least one of the region, the body tissue, and a disease name is included in the second attached data which are attached to the intelligent information; and at least one of the work assisting unit limits the range of assisting processes and the range of intelligent information to be utilized based on the data that identifies at least one of the region, the body tissue, and the disease name, the second attached information comprises at least an identity information of the disease name used to diagnose a patient, the work assisting units generate new pieces of intelligent information that indicate a correlation among different diseases in diseases corresponding to the identity information of the disease name which is included in the second attached information of the intelligent information to be utilized during the assisting process that assists the work of the medical workers, the intelligent information registering unit attaches the second attached data to the new pieces of intelligent information generated by the work assisting unit, and registers the pieces of intelligent information to which the second attached data are attached in the database, at least one of the plurality of intelligent information generating units, the intelligent information generation instructing unit, and the intelligent information registering unit comprise at least one hardware component, and the intelligent information registering unit generates one of a collective object that includes all pieces of intelligent information generated from a single image and a collective object that includes all pieces of intelligent information having common values in the second attached data, and registers the generated collective object in the database.

5. The system for promoting utilization of medical information as defined in claim 3, wherein:

the intelligent information registering unit generates one of a collective object that includes all pieces of intelligent information generated from a single image and a collective object that includes all pieces of intelligent information having common values in the second attached data, and registers the generated collective object in the database.

* * * * *